US012570588B2

(12) United States Patent
Koseoglu et al.

(10) Patent No.: US 12,570,588 B2
(45) Date of Patent: Mar. 10, 2026

(54) DISTILLATE HYDROCRACKING PROCESS WITH A REVERSE ISOMERIZATION STEP TO INCREASE A CONCENTRATION OF N-PARAFFINS

(71) Applicant: Saudi Arabian Oil Company, Dhahran (SA)

(72) Inventors: Omer Refa Koseoglu, Dhahran (SA); Ashok Kumar Punetha, Dhahran (SA)

(73) Assignee: Saudi Arabian Oil Company, Dhahran (SA)

(*) Notice: Subject to any disclaimer, the term of this patent is extended or adjusted under 35 U.S.C. 154(b) by 120 days.

(21) Appl. No.: 18/320,351

(22) Filed: May 19, 2023

(65) Prior Publication Data

US 2024/0383825 A1 Nov. 21, 2024

(51) Int. Cl.
*C07C 4/06* (2006.01)
*C10G 69/04* (2006.01)
*B01D 3/10* (2006.01)
*B01D 3/14* (2006.01)

(52) U.S. Cl.
CPC ............... *C07C 4/06* (2013.01); *C10G 69/04* (2013.01); *B01D 3/10* (2013.01); *B01D 3/143* (2013.01); *C10G 2300/1055* (2013.01); *C10G 2300/202* (2013.01); *C10G 2400/02* (2013.01); *C10G 2400/20* (2013.01); *C10G 2400/28* (2013.01)

(58) Field of Classification Search
None
See application file for complete search history.

(56) References Cited

U.S. PATENT DOCUMENTS

| | | | |
|---|---|---|---|
| 3,240,694 A | 3/1966 | Mason et al. | |
| 4,713,167 A | 12/1987 | Reno et al. | |
| 4,859,312 A * | 8/1989 | Miller .................... | B01J 29/85 |
| | | | 208/135 |
| 4,950,384 A | 8/1990 | Groeneveld et al. | |
| 5,026,472 A | 6/1991 | Hoehn et al. | |
| 5,139,647 A * | 8/1992 | Miller .................... | B01J 29/85 |
| | | | 208/18 |
| 5,885,440 A | 3/1999 | Hoehn et al. | |
| 5,904,835 A | 5/1999 | Thakkar | |

(Continued)

FOREIGN PATENT DOCUMENTS

WO 2021183323 A1 9/2021

*Primary Examiner* — Tam M Nguyen

(74) *Attorney, Agent, or Firm* — DINSMORE & SHOHL LLP

(57) ABSTRACT

In accordance with one or more embodiments of the present disclosure, a process for treating a diesel feedstock to convert diesel to component-paraffins includes hydrodesulfurizing and hydrodenitrogenizing the diesel feedstock to reduce a sulfur content of the diesel feedstock and a nitrogen content of the diesel feedstock; hydrocracking the hydrodesulfurized and hydrodenitrogenized diesel feedstock over a metal-containing diesel hydrocracking catalyst comprising at least one zeolite to produce a hydrocrackate fraction; separating the hydrocrackate fraction into a first stream enriched in n-paraffins and a second stream enriched in iso-paraffins and naphthenes; and reverse isomerizing at least a portion of the second stream over an isomerization catalyst to convert at least a portion of the iso-paraffins to n-paraffins, producing a reverse isomerate fraction.

20 Claims, 1 Drawing Sheet

(56)     References Cited

U.S. PATENT DOCUMENTS

| | | | |
|---|---|---|---|
| 6,113,775 | A | 9/2000 | Christolini et al. |
| 6,217,746 | B1 | 4/2001 | Thakkar et al. |
| 6,312,586 | B1 | 11/2001 | Kalnes et al. |
| 11,141,741 | B2 | 10/2021 | Vilagines et al. |
| 11,312,913 | B2 | 4/2022 | Koseoglu et al. |
| 11,473,022 | B2 | 10/2022 | Koseoglu et al. |
| 2013/0018113 | A1* | 1/2013 | Tasaka ..................... C10G 2/32 |
| | | | 518/728 |
| 2019/0218466 | A1* | 7/2019 | Slade ...................... C10L 1/026 |
| 2021/0277316 | A1 | 9/2021 | Funk et al. |

* cited by examiner

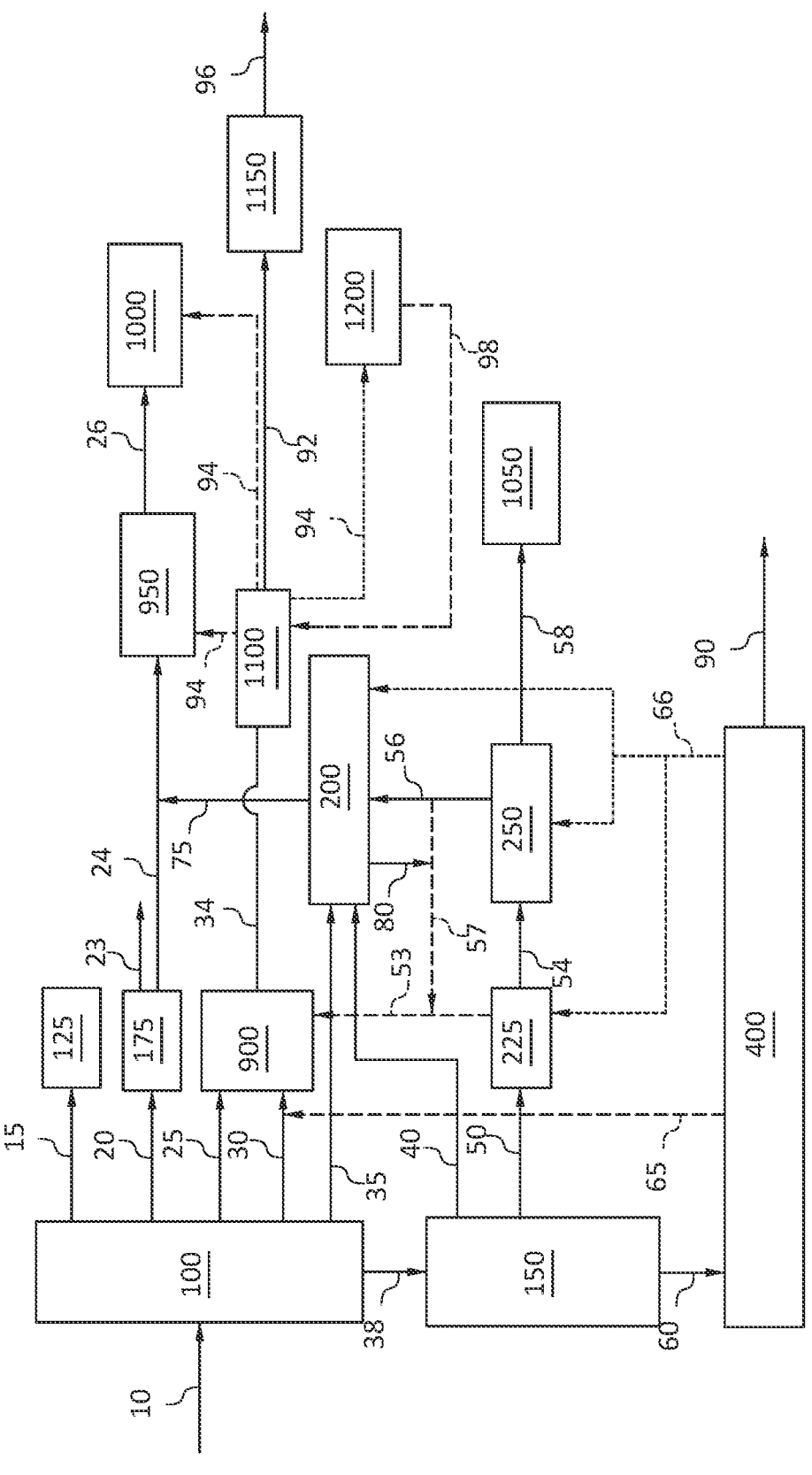

DISTILLATE HYDROCRACKING PROCESS WITH A REVERSE ISOMERIZATION STEP TO INCREASE A CONCENTRATION OF N-PARAFFINS

FIELD

Embodiments of the present disclosure generally relate to hydrocracking of hydrocarbon oil, and pertain particularly to a process for converting a diesel feedstock to produce value added products.

TECHNICAL BACKGROUND

Hydrocracking processes are used commercially in a large number of petroleum refineries to process a variety of hydrocarbon feeds boiling in the range of 370° C. to 520° C. in conventional hydrocracking units and boiling at 520° C. and above in residue hydrocracking units. In general, hydrocracking processes split the molecules of the hydrocarbon feed into smaller, i.e., lighter, molecules having higher average volatility and economic value. Additionally, hydrocracking processes typically improve the quality of the hydrocarbon feedstock by increasing the hydrogen-to-carbon ratio and by removing organosulfur and organonitrogen compounds. Current hydrocracking processes lead to a surplus of diesel, and market conditions drive research efforts to convert diesel into value added products, such as ethylene, propylene, butylene, and aromatics (benzene, toluene, and xylene).

SUMMARY

There is a continual need for more effective processes for converting diesel into value added products. It has been discovered that a process that includes hydrocracking diesel upstream of reverse isomerization of isoparaffins to n-paraffins may greatly enhance the effectiveness of converting the diesel into value added products.

According to at least one aspect of the present disclosure, a process for treating a diesel feedstock to convert diesel to n-paraffins can comprise hydrodesulfurizing and hydrodenitrogenizing the diesel feedstock to reduce a sulfur content of the diesel feedstock and a nitrogen content of the diesel feedstock, hydrocracking the hydrodesulfurized and hydrodenitrogenized diesel feedstock over a metal-containing diesel hydrocracking catalyst comprising at least one zeolite to produce a hydrocrackate fraction, separating the hydrocrackate fraction into a first stream enriched in n-paraffins and a second stream enriched in iso-paraffins and naphthenes, and reverse isomerizing at least a portion of the second stream over an isomerization catalyst to convert at least a portion of the iso-paraffins to n-paraffins, producing a reverse isomerate fraction.

Additional features and advantages of the embodiments described herein will be set forth in the detailed description which follows, and in part will be readily apparent to those skilled in the art from that description or recognized by practicing the embodiments described, including the detailed description and the claims which are provided infra.

BRIEF DESCRIPTION OF THE DRAWINGS

The following detailed description of specific embodiments of the present disclosure can be best understood when read in conjunction with the following drawings in which:

FIG. 1 depicts a process and system comprising hydrocracking unit(s), separator(s) and reverse isomerization unit(s) in accordance with one or more embodiments of the present disclosure.

DETAILED DESCRIPTION

In embodiments, a process for treating a diesel feedstock to convert diesel to a gasoline blending component includes hydrodesulfurizing and hydrodenitrogenizing the diesel feedstock to reduce a sulfur content of the diesel feedstock and a nitrogen content of the diesel feedstock; hydrocracking the hydrodesulfurized and hydrodenitrogenized diesel feedstock over a metal-containing catalyst comprising at least one zeolite to produce a hydrocrackate fraction; separating the hydrocrackate fraction into a first stream enriched in n-paraffins and a second stream enriched in iso-paraffins and naphthenes; and isomerizing at least a portion of the second stream over an isomerization catalyst to convert at least a portion of the iso-paraffins to n-paraffins, producing a reverse isomerate fraction. Embodiments will now be described in further detail.

As used herein, the term "hydrocarbon oil" or "hydrocarbon feedstock" refers to an oily liquid composed mostly of a mixture of hydrocarbon compounds. Hydrocarbon oil may include refined oil obtained from crude oil, synthetic crude oil, bitumen, oil sand, shale oil, or coal oil. The term "refined oil" includes, but is not limited to, vacuum gas oil (VGO), deasphalted oil (DAO) obtained from a solvent deasphalting process, demetallized oil (DMO), light and/or heavy coker gas oil obtained from a coker process, cycle oil obtained from a fluid catalytic cracking (FCC) process, and gas oil obtained from a visbreaking process.

As used herein, the term "hydrocarbon" refers to a chemical compound composed entirely of carbon and hydrogen atoms. An expression such as "$C_x$-$C_y$ hydrocarbon" refers to a hydrocarbon having from x to y carbon atoms. For instance, a $C_1$-$C_5$ hydrocarbon includes methane, ethane, propane, butanes, including iso-propane, butane, iso-butane, t-butane, and the pentanes.

As used herein, the term "diesel" refers to a middle distillate, largely produced from fractional distillation of crude oil between 180° C. and 370° C. Compositionally, diesel may include $C_9$-$C_{25}$ hydrocarbons, with a majority of the constituents being $C_{12}$-$C_{20}$, by weight. As used herein, the term "diesel feedstock" refers to a liquid composed mostly of diesel.

As used herein, the term "hydrogen/oil ratio" or "hydrogen-to-oil ratio" refers to a standard measure of the volume rate of hydrogen circulating through the reactor with respect to the volume of feed. The hydrogen/oil ratio may be determined by comparing the flow volume of the hydrogen gas stream and the flow volume of the hydrocarbon feed using standard flow meters.

As used herein, the term "liquid hourly space velocity" or "LHSV" refers to the ratio of the liquid flow rate of the hydrocarbon feed to the catalyst volume or mass.

As used herein, the term "research octane number" or "RON" refers to a property of fuels that is related to the amount of compression the fuel can withstand before detonating. RON can be determined using ASTM D2700, Standard Test Method for Motor Octane Number of Spark-Ignition Engine Fuel.

As used herein, the term "activity of the catalyst" or "catalytic activity" refers to the increase in the rate of the hydrocracking process due to the presence of the catalyst and may be approximated by the temperature at which 50% conversion of the feedstock is converted. A more highly active catalyst will have a lower such temperature.

Embodiments in accordance with the present disclosure generally relate to a process and system that includes converting and upgrading a middle distillate oil feedstock. As used herein, a middle distillate refers to a range of refined petroleum products obtained in the "middle" boiling range from about 180° C. to about 370° C. during the processing of crude oil. These processes may include hydrocracking the middle distillate oil feedstock over a metal catalyst to produce a hydrocrackate fraction. In one or more embodiments, the distillate oil feedstock may be hydrodesulfurized and/or hydrodenitrogenized prior to being hydrocracked in order to reduce the sulfur and nitrogen content of the middle distillate oil feedstock. In one or more embodiments, the hydrocrackate fraction may be separated into a first stream enriched in n-paraffins and a second stream enriched in iso-paraffins and naphthenes. In one or more embodiments, at least a portion of the second stream may be reverse isomerized over an isomerization catalyst to convert at least a portion of the iso-paraffins to n-paraffins.

Thus, embodiments of the present disclosure are directed to converting diesel to value added products. Because diesel is a desirable fuel, it is not conventionally hydrocracked or catalytically cracked. Rather, conventional hydrocracking processes were developed to convert heavy oil fractions as opposed to middle distillate fractions due to the high demand for middle distillates such as diesel oil. Therefore, considering that there will be a diesel surplus in the market and growing demand for chemicals, the present disclosure advantageously provides for the conversion of diesel to gasoline and/or high quality gasoline blending products, such as isomerate and aromatics rich gasoline, through hydrocracking.

As noted above, diesel is a middle distillate, largely produced from fractional distillation of crude oil between 180° C. and 370° C. Compositionally, diesel may include $C_9$-$C_{25}$ hydrocarbons, with a majority of the constituents being $C_{12}$-$C_{20}$, by weight. However, it is also envisioned that the hydrocracker feed of the present disclosure may more broadly encompass distillates that boil in the range of 100° C. to 420° C., such as having a lower limit of 100° C., 150° C. 180° C., or 200° C., and an upper limit of any of 350° C. 360° C. 375° C., 400° C., and 420° C. Such distillates are commonly referred to as distillates. While diesel is largely produced from distillation from 180° C. to 370° C., diesel is also produced from heavier fractions by cracking, including atmospheric gas oils, vacuum gas oils, and coker distillates, and it is envisioned that the feed to the hydrocracker may include downstream products from cracking of atmospheric gas oils, vacuum gas oils, and coker distillates. However, it is also appreciated that lighter fractions may also form part of the present feed. Thus, in one or more embodiments, the feed to a hydrocracker, as described herein, may be a feed that has been previously processed to arrive at the feed to the hydrocracker described herein. For example, for a majority of diesel that is produced from a middle distillate fractioned from 150° C. to 420° C., from 200° C. to 360° C., or from 250° C. to 350° C., such distillate may be hydrotreated prior to feeding the middle distillate to a hydrocracker.

In one or more embodiments, the middle distillates (distillates between 150° C. and 420° C. or between 200° C. and 360° C.) from the fractional distillation of crude oil are used as the feedstream for the hydrocracker. The middle distillates may be sent to a two-stage hydrotreating unit having hydrotreating in a first stage and hydrocracking in a second stage. The hydrotreating may be performed in the presence of a hydrotreating catalyst to significantly reduce the sulfur and nitrogen content of the feedstock, which may be referred to as desulfurization (or hydrodesulfurization) and denitrogenation (or hydrodenitrogenation). During hydrotreating processes, unsaturated hydrocarbons such as olefins, alkynes, and aromatics may also become saturated through reaction with hydrogen. Following hydrotreating and prior to hydrocracking, $H_2S$ and $NH_3$ produced in the hydrodesulfurization and hydrodenitrogenation may be separated from the hydrotreated effluent along with any light gases and/or light components boiling in naphtha range. The remaining effluent may be directed to the hydrocracker. In one or more embodiments, the effluent's sulfur content is less than or equal to 500 ppm by weight or less than or equal to 50 ppm by weight or less than or equal to 10 ppm by weight.

Further, in one or more embodiments, it is also envisioned that the feedstock may also include components that were processed from a heavier distillate that was subjected to one or more processing steps, such as vacuum gas oil being subjected to catalytic hydrocracking or fluid catalytic cracking, to arrive at a feed for the present hydrocracking. Thus, it is envisioned that the feed to the present hydrocracking may include, in addition to middle distillates (as described above), downstream products from atmospheric gas oils, vacuum gas oils, and coker distillates from cracking. For example, it is envisioned that the feed may include the diesel pool formed in a conventional refinery.

The hydrocracking processes generally break the molecules of a feedstock (whether limited to middle distillates or including downstream products from heavier distillates) into smaller, i.e. lighter, molecules having higher average volatility and economic value than the feedstock. Thus, hydrocracking processes in accordance with the present disclosure generally comprise combining a distillate oil feed, such as described above, with hydrogen gas, and subjecting the mixture to elevated temperatures in the presence of a hydrocracking catalyst.

In one or more embodiments, the hydrocracking catalyst may include a zeolite, a post modified zeolite, a metal containing zeolite, active phase metals, a binder or support, or a combination of two or more thereof. For example, the hydrocracking catalyst may include an ultra-stable Y-type (USY) zeolite, a post modified USY zeolite (FAU zeolite), a zeolite beta (BEA zeolite), an MFI zeolite, an MOR zeolite, or a combination of two or more thereof. Active phase metals may include noble metals, i.e., Ru, Rh, Pd, Ag, Os, Ir, Pt, and Au. In embodiments, the metal containing zeolite comprises more than one such metal. In embodiments, the noble metals include Pt, Pd, or a mixture of Pt and Pd. An unsupported metal catalyst according to the present disclosure may include an active phase material including, in certain embodiments, Ni, W. Mo, Co, or a combination of two or more thereof. In embodiments, the binder may include alumina, silica, titania, or combination of two or more thereof.

In one or more embodiments, the hydrocracking may occur in a hydrocracking reactor that operates at a temperature from 250° C. to 450° C., from 300° C. to 400° C., from 280° C. to 400° C., or from 280° C. to 370° C. In one or more embodiments, the hydrocracking may occur in a hydrocracking reactor that operates at a hydrogen partial pressure of less than or equal to 90 bars, less than or equal to 80 bars, less than or equal to 70 bars, or less than or equal to 60 bars. In one or more embodiments, the hydrocracking may occur in a hydrocracking reactor that operates with a liquid hourly space velocity LHSV from 0.1 $h^{-1}$ to 10 $h^{-1}$, from 0.25 h$^{-1}$ to 5 h$^{-1}$, from 0.5 h$^{-1}$ to 5 h$^{-1}$, or from 0.5 h$^{-1}$ to 2 h$^{-1}$. In one or more embodiments, the hydrocracking may occur in a hydrocracking reactor that operates with a hydrogen/oil ratio from 500 standard liters per liter (StLt/Lt) to 2500 StLt/Lt, from 500 StLt/Lt to 1000 StLt/Lt, from 800 StLt/Lt to 2000 StLt/Lt, or from 1000 StLt/Lt to 1500 StLt/Lt.

In accordance with one or more embodiments, the hydrocracking process is accomplished over a metal catalyst, such as those described above to convert the middle distillate feedstock, such as a diesel oil feedstock, to a hydrocrackate fraction stream as gasoline blending components. In one or more embodiments, the hydrocracked effluent may be a product stream comprising gasoline blend components, where the produced product stream has an octane number greater than or equal to 55, greater than or equal to 60, or greater than or equal to 70. This hydrocrackate fraction may be further processed to obtain value-added materials.

In accordance with one or more embodiments, the process for treating a feedstock includes separating the hydrocrackate fraction into a first stream enriched in n-paraffins and a second stream enriched in iso-paraffins and naphthenes. As used herein, the phrase "stream enriched in n-paraffins" refers to a stream comprising at least 30 weight percent n-paraffins, based on the total weight of the stream enriched in n-paraffins. As used herein, the phrase "stream enriched in iso-paraffins" refers to a stream comprising at least 30 weight percent iso-paraffins, based on the total weight of the stream enriched in iso-paraffins. The first stream and the second stream may be separated from one another using an adsorption/desorption process, such as those disclosed in U.S. Pat. Nos. 4,176,053; 4,476,345; and 5,863,315; the entire content of each of which is incorporated herein by reference. In a typical process, the hydrocrackate fraction is allowed to flow over an adsorbent capable of retaining n-paraffins while allowing iso-paraffins to pass through. For instance, a zeolitic molecular sieve may be used as the adsorbent. The n-paraffins may then be desorbed from the adsorbent using a non-sorbable purge gas under controlled pressure and/or temperature conditions. For instance, desorption pressure may be from 0.3 MPa to 3 MPa, and desorption temperature may be from 170° C. to 400° C.

In accordance with one or more embodiments, the process for treating a feedstock includes reverse isomerizing at least a portion of the second stream enriched in iso-paraffins over an isomerization catalyst to convert at least a portion of the iso-paraffins to n-paraffins, producing a reverse isomerate fraction.

In accordance with one or more embodiments, the isomerizing process is accomplished over a metal catalyst. In embodiments, the isomerization catalyst may comprise platinum. In embodiments, the isomerization catalyst may comprise an acidic component. In embodiments, the acidic component of the isomerization catalyst may comprise chlorinated alumina, sulfated zirconia, mordenite framework zeolite (MOR), or combinations thereof. In embodiments, the isomerization catalyst consists of, consists essentially of, or comprises Pt/Cl/Al$_2$O$_3$, Pt/SO$_4^{2-}$, Pt/MOR, or a combination of two or more therefrom.

In accordance with one or more embodiments, the process for treating a feedstock includes combining at least a portion of the reverse isomerate fraction with at least a portion of the hydrocrackate fraction. In embodiments, the reverse isomerate fraction is separated into a third stream enriched in n-paraffins and a fourth stream enriched in iso-paraffins and naphthenes. The third stream and the fourth stream may be separated from one another using an adsorption/desorption process, such as those disclosed in U.S. Pat. Nos. 4,176,053; 4,476,345; and 5,863,315. In a typical process, the reverse isomerate fraction is allowed to flow over an adsorbent capable of retaining n-paraffins while allowing iso-paraffins to pass through. For instance, a zeolitic molecular sieve may be used as the adsorbent. The n-paraffins may then be desorbed from the adsorbent using a non-sorbable purge gas under controlled pressure and/or temperature conditions. For instance, desorption pressure may be from 0.3 MPa to 3 MPa, and desorption temperature may be from 170° C. to 400° C.

Referring now to FIG. 1, a process flow diagram according to one or more embodiments of the present disclosure is shown. While the present disclosure focuses on the upgrading of diesel by hydrocracking, separation of the resulting hydrocrackate stream, (as described above), the present FIGURE is provided to show the modifications that can be made to an existing refinery to convert hydrotreating units to perform the presently described hydrocracking to convert diesel surplus into value added products, such as gasoline.

As shown in the FIGURE, crude oil 10 is introduced to distillation column 100. Crude oil 10 may be any source of crude oil and distillation column 100 can be any type of separation unit capable of separating a hydrocarbon stream (specifically crude oil 10) into component parts, based on targeted cut points of distillation. An example of distillation column 100 includes an atmospheric distillation column. Distillation column 100 can be operated to separate acid gas, naphtha, kerosene/jet, (light) gas oil, and atmospheric residue 38 that may be directed to vacuum distillation column 150. Vacuum distillation column 150 can be employed to separate vacuum gas oils such as light vacuum gas oil, heavy vacuum gas oil, and vacuum residue, under vacuum conditions.

As shown in the FIGURE, distillation column 100 can produce, for example, acid gas 15, light fraction (naphtha) stream 20, jet/kerosene 25, light gas oil 30, heavy gas oil 35, and atmospheric residue 38. Vacuum distillation column 150 can produce, for example, light vacuum gas oil 40, heavy vacuum gas oil 50, and vacuum residue stream 60 from the atmospheric residue 38. In one or more embodiments light fraction stream 20 can have a T95% cut point of less than or equal to 240° C. As used herein, the term "T95% cut point" refers to the temperature at which at least 95% of the fraction has evaporated. Light fraction stream 20 may contain naphtha. Acid gas stream 15 may be distilled and directed to a gas treating unit 125. Acid gas generated during crude oil and natural gas processing typically includes hydrogen sulfide and other undesirable compounds. The removal of acid gas via acid gas stream 15 reduces components such as hydrogen sulfide, carbon dioxide (CO$_2$), carbonyl sulfide (COS), carbon disulfide (CS$_2$) and mercaptans (RSH) from gas and liquid hydrocarbon streams.

Light fraction stream 20 may be directed to a naphtha hydrotreating unit 175 to produce a heavy naphtha stream 23 and a light naphtha stream 24. Light naphtha stream 24 is directed to an isomerization unit 950 to produce isomerate product stream 26 that is then introduced to gasoline pool 1000. Heavy naphtha stream 23 may be directed to a catalytic reforming unit.

Jet/kerosene stream 25 may have a cut point in the range of 180° C. to 260° C., for example, and light gas oil 30 can have a T95% cut point in the range between 340° C. and 380° C. The jet/kerosene stream 25 and light gas oil stream 30 are each directed to diesel hydrocracking unit 900. While jet/kerosene stream 25 and light gas oil stream 30 would conventionally be directed to a jet/diesel hydrotreater for hydrodesulfurization and hydrodenitrogenation to reduce the sulfur and/or nitrogen content prior to feeding the effluent into a diesel pool, in accordance with embodiments of the present disclosure, jet/kerosene stream 25 and light gas oil stream 30 may instead be directed to diesel hydrocracking unit 900. Diesel hydrocracking unit 900 comprises a hydrotreating reactor, separation unit, and hydrocracking reactor. The separation unit may include, for example, a flash drum, gas-liquid separators and/or stripping columns and/or fractionation to remove dissolved gases such as hydrogen sulfide and ammonia from the hydrotreated effluent.

In the first stage of the diesel hydrocracking unit 900, the jet/kerosene stream 25 and light gas oil 30 are subjected to hydrodesulfurization and hydrodenitrogenation in the hydrotreating reactor to reduce and/or remove sulfur and nitrogen. In one or more embodiments of the present disclosure, a hydrotreating reactor may operate at temperatures in the broad range from 250° C. to 450° C. or from 300° C. to 450° C. Reaction zone pressures may be in the range from 25 bar to 150 bar, and the hydrogen partial pressure may be from 35 bar to 100 bar. Contact times usually correspond to liquid hourly space velocities (LHSV) in the range from 0.2 $hr^{-1}$ to 6.0 $hr^{-1}$ or from 0.2 $hr^{-1}$ to 4.0 $hr^{-1}$. The space velocity may be dependent upon the feedstock composition. In embodiments, the hydrotreating reactor may operate at a hydrogen-to-oil ratio of from 100 standard liters per liter (StLt/Lt) to 600 StLt/Lt, such as from 200 StLt/Lt to 400 StLt/Lt.

In one or more embodiments of the present disclosure, the hydrotreating catalyst may be any suitable catalyst. Hydrotreating catalysts of some embodiments may comprise one or more metals selected from the group consisting of molybdenum, tungsten, cobalt, and nickel. The active metals may be supported to provide a greater surface area. More than one type of hydrotreating catalyst may be used in the same reactor. In some embodiments, that are not shown, multiple hydrotreating reactors may be used in series within a unit 900. In embodiments where multiple hydrotreating reactors are used, each reactor may be primarily directed to the removal of a different component, such as hydrodesulfurization and hydrodenitrogenation.

In certain embodiments in which an objective is hydrodenitrogenation, alumina or silica-alumina based catalysts loaded with Ni—Mo or Co—Mo active metals, or combinations thereof, are used. In embodiments in which the objective is to remove nitrogen and to increase the conversion of hydrocarbons, silica, alumina, titania, zeolite, or a combination of two or more thereof are used as catalysts, with active metals including Ni—Mo, Co—Mo, or combinations thereof.

In diesel hydrocracking unit 900, the hydrotreated effluent stream comprising hydrotreated products from jet/kerosene stream 25 and light gas oil stream 30 may be directed to a separating unit where additional $H_2S$, $NH_3$, any light gases including $C_1$-$C_4$ hydrocarbons, and any naphtha may be removed. The separated effluent, including fractions with an initial nominal boiling point temperature of about 180° C. and final boiling point temperatures ranging from about 340° C. to about 420° C., is sent to the hydrocracking reactor to undergo cracking reactions. The hydrocracking reactor may include a zeolite, a post modified zeolite, a metal containing zeolite, active phase metals, a binder or support, or a combination of two or more thereof.

The hydrocracking in the diesel hydrocracking unit 900 may be performed at a reaction temperature from 250° C. to 450° C., from 300° C. to 400° C., or from 280° C. to 370°

C. In one or more embodiments, the hydrocracking may occur in a hydrocracking reactor that operates at a hydrogen partial pressure of less than or equal to 100 bars, less than or equal to 90 bars, less than or equal to 80 bars, less than or equal to 70 bars, or less than or equal to 60 bars. In one or more embodiments, the hydrocracking may occur in a hydrocracking reactor that operates with a liquid hourly space velocity LHSV from 0.1 $h^{-1}$ to 10 $h^{-1}$, from 0.25 $h^{-1}$ to 5 $h^{-1}$, from 0.5 $h^{-1}$ to 5 $h^{-1}$, or from 0.5 $h^{-1}$ to 2 $h^{-1}$. In one or more embodiments, the hydrocracking may occur in a hydrocracking reactor that operates with a hydrogen/oil ratio from 500 standard liters per liter (StLt/Lt) to 2500 StLt/Lt, from 800 StLt/Lt to 2000 StLt/Lt, or from 1000 StLt/Lt to 1500 StLt/Lt.

After the second stage (hydrocracking) of diesel hydrocracking unit 900, a hydrocrackate fraction 34, including n-paraffins, iso-paraffins, naphthenes, and aromatics, may be fed to separation zone 1100, which separates the hydrocrackate fraction 34 into an n-paraffin-rich stream 92 and an iso-paraffin-rich stream 94. In embodiments, the n-paraffin-rich stream 92 may comprise of from 50 wt. % to 99 wt. % n-paraffins, such as from 60 wt. % to 99 wt. %, from 70 wt. % to 99 wt. %, from 80 wt. % to 99 wt. %, or from 85 wt. % to 99 wt. % n-paraffins, based on the total weight of the n-paraffin-rich stream 92. In embodiments, the n-paraffin-rich stream 92 comprises less than 10 wt. %, less than 9 wt. %, less than 8 wt. %, or less than 7 wt. % iso-paraffins, based on the total weight of the n-paraffin-rich stream 92. The n-paraffin-rich stream 92 may be fed to steam cracking unit 1150 to produce light olefin stream 96. In embodiments, the iso-paraffin-rich stream 94 may comprise of from 30 wt. % to 99 wt. % iso-paraffins, such as from 40 wt. % to 80 wt. %, from 40 wt. % to 70 wt. %, from 50 wt. % to 80 wt. %, or from 50 wt. % to 70 wt. % iso-paraffins, based on the total weight of the iso-paraffin-rich stream 94. In embodiments, the iso-paraffin stream 94 comprises less than 5 wt. %, less than 4 wt. %, less than 3 wt. %, less than 2 wt. %, or less than 1 wt. % n-paraffins, based on the total weight of the iso-paraffin-rich stream 94. The iso-paraffin-rich stream 94 may be directed to reforming/isomerization unit 950 prior to being directed to gasoline pool 1000, sent directly to gasoline pool 1000, or sent to reverse isomerization unit 1200 to produce effluent 98, which may include a reverse isomerate fraction including n-paraffins, iso-paraffins, naphthenes, and aromatics. In embodiments, the iso-paraffin-rich stream may be sent to diesel hydrocracking unit 900, which may convert napthenic hydrocarbons and reduce build-up of napthenic hydrocarbons in the system (not pictured).

In reverse isomerization unit 1200, the iso-paraffin-rich stream 94 may be isomerized to increase a concentration of n-paraffins and decrease a concentration of iso-paraffins, producing effluent 98 comprising the reverse isomerate fraction.

The isomerization in reverse isomerization unit 1200 may be performed at a reaction temperature of from 80° C. to 400° C., such as from 80° C. to 300° C., from 80° C. to 200° C., from 100° C. to 400° C., from 100° C. to 300° C., or from 100° C. to 200° C. The isomerization in reverse isomerization unit 1200 may be performed at a pressure range of from 1 bar to 80 bar, such as from 1 bar to 50 bar, 1 bar to 35 bar, or from 15 bar to 35 bar. The isomerization in reverse isomerization unit 1200 may be performed at a LHSV of from 0.5 $h^{-1}$ to 8 $h^{-1}$, such as from 0.5 $h^{-1}$ to 5 $h^{-1}$, from 0.5 $h^{-1}$ to 2 $h^{-1}$, or from 1 $h^{-1}$ to 2 $h^{-1}$. The isomerization in reverse isomerization unit 1200 may be performed at a hydrogen to hydrocarbon ratio of from 100 StLt/Lt to 1000 StLt/Lt, such as from 100 StLt/Lt to 500 StLt/Lt, or from 100 StLt/Lt to 200 StLt/Lt. In embodiments, the iso-paraffin-rich stream may comprise less than 2 wt. % aromatics.

The reverse isomerate fraction, produced from the reverse isomerization unit 1200, may be fed to separation zone 1100. In embodiments, the reverse isomerate fraction may be combined with hydrocrackate fraction 34, and the combined effluent comprising hydrocrackate fraction 34 and the reverse isomerate fraction of effluent 98 may be fed to separation zone 1100 (not pictured). The reverse isomerate fraction of the effluent 98 may be directed to a separating unit where light gases including $C_1$-$C_4$ hydrocarbons, and naphtha may be removed prior to feeding the reverse isomerate fraction of the effluent 98 to the separation zone 1100 or prior to combining the reverse isomerate fraction with hydrocrackate fraction 34 (not pictured).

After feeding at least a portion of the reverse isomerate fraction to the separation zone 1100, the reverse isomerate fraction of the effluent 98 may be separated into a third stream enriched in n-paraffins and a fourth stream enriched in iso-paraffins. In embodiments, the third stream enriched in n-paraffins comprises at least a portion of the n-paraffin-rich stream 92 from the hydrocrackate fraction and n-paraffins from the reverse isomerate fraction. In embodiments, at least a portion of the third stream enriched in n-paraffins is combined with at least a portion of the n-paraffin-rich stream 92. In embodiments, the fourth stream enriched in iso-paraffins comprises at least a portion of the iso-paraffin-rich stream 94 from the hydrocrackate fraction and iso-paraffins from the reverse isomerate fraction. In embodiments, at least a portion of the fourth stream enriched in iso-paraffins is combined with at least a portion of the iso-paraffin-rich stream 94. In embodiments, the process may include a distillation step to distill at least a portion of the fourth stream enriched in iso-paraffins to separate aromatics and naphthenes from the iso-paraffins. In embodiments, the process may include a bleed stream to bleed iso-paraffins from the fourth stream enriched in iso-paraffins to reduce a buildup of aromatics and naphthenes during one or more reverse isomerization and recycle steps.

In embodiments, the third stream enriched in n-paraffins may comprise at least 50 wt. %, at least 60 wt. %, at least 70 wt. %, at least 80 wt. %, at least 90 wt. %, or at least 95 wt. % n-paraffins, based on the total weight of the third stream. In embodiments, the third stream enriched in n-paraffins may comprise of from 50 wt. % to 99 wt. % n-paraffins, such as from 60 wt. % to 99 wt. %, from 70 wt. % to 99 wt. %, from 80 wt. % to 99 wt. %, or from 85 wt. % to 99 wt. % n-paraffins, based on the total weight of the third stream enriched in n-paraffins. In embodiments, the third stream enriched in n-paraffins comprises less than 10 wt. %, less than 9 wt. %, less than 8 wt. %, or less than 7 wt. % iso-paraffins, based on the total weight of the third stream enriched in n-paraffins. In embodiments, the third stream enriched in n-paraffins may comprise at least 30 wt. %, at least 35 wt. %, or at least 40 wt. % n-paraffins, based on the total weight of the hydrocrackate fraction. Without intending to be bound by any particular theory, it is believed that processes including a reverse isomerization of at least a portion of the iso-paraffin-rich stream 94 from the hydrocrackate fraction to form the reverse isomerate fraction, followed by introduction of at least a portion of the reverse isomerate fraction to the separator 1100 may result in an increased concentration of n-paraffins produced.

In embodiments, the fourth stream enriched in iso-paraffins may comprise of from 30 wt. % to 99 wt. % iso-paraffins, such as from 40 wt. % to 80 wt. %, from 40 wt. % to 70 wt. %, from 50 wt. % to 80 wt. %, or from 50 wt. % to 70 wt. % iso-paraffins, based on the total weight of the fourth stream enriched in iso-paraffins. In embodiments, the fourth stream enriched in iso-paraffins comprises less than 5 wt. %, less than 4 wt. %, less than 3 wt. %, less than 2 wt. %, or less than 1 wt. % n-paraffins, based on the total weight of the iso-paraffin-rich stream 94.

The third stream enriched in n-paraffins may be fed to steam cracking unit 1150 to produce a light olefin stream. The fourth stream enriched in iso-paraffins may be directed to isomerization unit 950 prior to being directed to gasoline pool 1000, sent directly to gasoline pool 1000, or sent to reverse isomerization unit 1200 to further increase a concentration of n-paraffins. This recycling process of reverse isomerizing a stream comprising iso-paraffins and feeding at least a portion of the reverse isomerized product to separation zone 1100 may be repeated any number of times to further increase a concentration of n-paraffins produced.

Light vacuum gas oil 40 may have a T95% cut point in the range from 400° C. to 430° C. Light vacuum gas oil 40 can be introduced to cracking unit 200, which may be selected from, for example, a catalytic hydrocracking unit, a fluid catalytic cracking unit, and the like. Hydrocracking unit 200 may also receive heavy gas oil 35. The effluent may be fractionated by fractionator unit of hydrocracking unit 200 into light fraction 75 and gas oil 80. Upgraded light fraction 75 may contain the naphtha range hydrocarbons and kerosene range hydrocarbons present in light vacuum gas oil 40. Upgraded light fraction 75 may be mixed with treated light fraction stream 24 and introduced to isomerization unit 950 prior to being directed to gasoline pool 1000. In at least one embodiment, upgraded light fraction 75 may be introduced to gasoline 1000 without first mixing with treated light fraction stream 24.

Heavy vacuum gas oil 50 may have a T95% cut point of greater than or equal to 565° C. Vacuum residue stream 60 may have a T5% cut point of greater than or equal to 565° C. Vacuum residue stream 60 contains the heaviest fraction of crude oil. Heavy vacuum gas oil 50 may be introduced to vacuum gas oil hydrotreater 225 which may comprise a hydrotreating reactor and separator. The produced effluent from the hydrotreating reactor of hydrotreating unit 225 may be separated to remove gas oils which may be directed to the diesel hydrocracking reactor 900 via stream 53. Treated heavy vacuum gas oil stream 54 may be fed to catalytic cracking unit 250, which may be, for example, a fluid catalytic cracking unit, etc. The effluent of catalytic cracker 250, which may include cycle oils, for example, may be separated into catalytically cracked gasoline stream 58 and light cracked distillate stream 56. Catalytically cracked gasoline stream 58 may then be fed to hydrocracked gasoline pool 1050 and light and heavy cracked distillate stream 56 may be fed to hydrocracker 200 with light vacuum gas oil stream 40. In one or more embodiments, light cracked distillate stream 56 may be fed directly to diesel hydrocracking unit 900 via stream 57.

Vacuum residue stream 60 may be introduced to resid (residual) upgrading unit 400. Resid upgrading unit 400 may be any process unit capable of upgrading a heavy fraction stream. Examples of resid upgrading unit 400 include resid fluid catalytic cracking (RFCC) unit, residue hydrocracker, resid hydrodesulfurization (RHDS) hydrotreater, visbreaker, coker, gasifier, and solvent extractor. Resid upgrading unit 400 may produce resid upgraded product 90 and gas oil stream 65 which may be directed to diesel hydrocracking unit 900. Gas oil stream 65 may be directed to diesel hydrocracking unit 900 to be subjected to the hydrotreating, separation, and hydrocracking steps described above.

Vacuum gas oil stream 66 may be directed to diesel hydro-cracking unit 900 to be subjected to the hydrotreating, separation, and hydrocracking steps described above.

EXAMPLES

Using embodiments described above, an exemplary hydrocracking pilot plant test was conducted, as follows. The following examples are merely illustrative and should not be interpreted as limiting the scope of the present disclosure.

Comparative Example 1

A hydrocracking pilot plant test was conducted using a hydrodesulfurized diesel oil as a feedstock. The properties of the feedstock and simulated distillation of the of the feedstock are shown in Table 1.

TABLE 1

| Comparative Example 1 Feedstock Properties | |
| --- | --- |
| Property | Value |
| Density @ 15.6° C. (g/cm³) | 0.83 |
| Sulfur content (ppm by weight) | <10 |
| Nitrogen content (ASTM D-4629) (ppm by weight) | 21 |
| Simulated Distillation (D2887) | Temperature (° C.) |
| 0 wt. % | 110 |
| 5 wt. % | 177 |
| 10 wt. % | 203 |
| 30 wt. % | 255 |
| 50 wt. % | 287 |
| 70 wt. % | 318 |
| 90 wt. % | 362 |
| 95 wt. % | 379 |
| 100 wt. % | 414 |
| 2D GC × GC Composition | wt. % |
| Paraffins | 52.68 |
| Naphthenes | 25.26 |
| Mono-aromatics | 19.45 |
| Di-aromatics | 2.11 |
| Tri-Plus aromatics | 0.50 |

The experiments were conducted at 60 bars of hydrogen partial pressure, a temperature of 355° C., a LHSV of 1 h$^{-1}$, and a hydrogen to gas oil ratio of 1,000 StLt/Lt. The catalyst included platinum as the active-phase metal and the support included alumina and a post-modified USY zeolite comprising titanium and zirconium in the framework of the USY zeolite.

The diesel oil feedstock of Comparative Example 1 and simulated product distillation data are shown in Table 2. The diesel is fully converted to a hydrocrackate fraction comprising gasoline range products, as evidenced by the final boiling point of the product of 186° C., which is the expected boiling point for gasoline.

TABLE 2

| Comparative Example 1 Product Data | | |
| --- | --- | --- |
| Concentration Off | Feedstock Temperature (° C.) | Product Temperature (° C.) |
| 0 wt. % | 110 | 34 |
| 5 wt. % | 177 | 59 |

TABLE 2-continued

| Comparative Example 1 Product Data | | |
| --- | --- | --- |
| Concentration Off | Feedstock Temperature (° C.) | Product Temperature (° C.) |
| 10 wt. % | 203 | 69 |
| 30 wt. % | 255 | 89 |
| 50 wt. % | 287 | 103 |
| 70 wt. % | 318 | 119 |
| 90 wt. % | 362 | 141 |
| 95 wt. % | 379 | 149 |
| 100 wt. % | 414 | 186 |

Two-dimensional gas chromatography (2D GC×GC) was used to identify the n-paraffins, iso-paraffins, olefins, naphthenes, and aromatics. Under this analysis, the n-paraffins and iso-paraffins combined accounted for 76.9 wt. % of the products, naphthenes accounted for 22 wt. %, and aromatics accounted for 1 wt. %. The products were also analyzed for compositional type using PIONA (paraffin, isoparaffin, olefin, naphthene, aromatic) analysis, in accordance with ASTM D6730, and a research octane number (RON) of 64.5 was calculated from this data. As shown in Table 3, under the PIONA analysis, n-paraffins accounted for 14.3 wt. % of the products, iso-paraffins accounted for 52.1 wt. %, naphthenes accounted for 28.8 wt. %, and aromatics accounted for 3.5 wt. %. Thus, the process of Comparative Example 1 may sufficiently serve to simultaneously hydrocrack the diesel oil feedstock, hydrogenate the aromatics to naphthenes, crack naphthenes, and subsequently isomerize naphthenes to result in a final hydrocrackate fraction with greater than or equal to 50 wt. % iso-paraffins.

TABLE 3

| PIONA of the Hydrocrackate Fraction of Comparative Example 1 | | | | |
| --- | --- | --- | --- | --- |
| Column No. | n-Paraffins (wt. %) | iso-paraffins (wt. %) | Naphthenes (wt. %) | Aromatics (wt. %) |
| 3 | 0.006 | 0 | 0 | 0 |
| 4 | 0.044 | 0.061 | 0 | 0 |
| 5 | 0.352 | 0.539 | 0.385 | 0 |
| 6 | 4.144 | 6.281 | 4.303 | 0.708 |
| 7 | 4.983 | 18.714 | 16.066 | 1.3 |
| 8 | 3.832 | 17.046 | 5.346 | 0.966 |
| 9 | 0.991 | 9.069 | 3.007 | 0.464 |
| 10 | 0.183 | 1.058 | 0.087 | 0.063 |
| Total | 14.53 | 52.77 | 29.19 | 3.51 |

Comparative Example 2

The hydrocrackate fraction produced in Comparative Example 1 was subjected to an n-paraffin separation step in accordance with the process and reactor system described above. Adsorptive separation can be simulated according to methods known in the art. Adsorbents can include any adsorbents known in the art, such as shape selective adsorbent materials including molecular sieve and porous materials. Two fractions were obtained: 1. n-paraffin rich stream, 2. iso-paraffin rich stream. Table 4 summarizes the PIONA data for the hydrocrackate fraction, the n-paraffin rich stream, and the iso-paraffin rich stream. As shown in table 4, Comparative Example 2 only includes 14.24 wt. % n-paraffins in the n-paraffin rich stream, relative to the total weight of the hydrocrackate fraction. The iso-paraffin rich stream includes 51.71% iso-paraffins, relative to the total weight of the hydrocrackate fraction.

TABLE 4

| Comparative Example 2 Stream Data from Separation of Hydrocrackate Fraction | | | |
|---|---|---|---|
| Stream | Hydrocrackate fraction | First n-paraffin rich stream | First iso-paraffin rich stream |
| n-paraffins, wt. % | 14.53 | 14.24 | 0.29 |
| iso-paraffins, wt. % | 52.77 | 1.06 | 51.71 |
| Naphthenes, wt. % | 29.19 | 0.58 | 28.61 |
| Aromatics, wt. % | 3.45 | 0.07 | 3.38 |
| Total wt. % | 99.94 | 15.95 | 83.99 |

Example 1

The iso-paraffin rich stream of the hydrocrackate fraction produced in Comparative Example 2 was subjected to a reverse isomerization step in a fixed-bed reactor in accordance with the process and system described in this disclosure to yield a reverse isomerate fraction. The experiments were conducted at a temperature of 100° C., pressure of 50 bars, and a LHSV of 1.6 h$^{-1}$ over an isomerization catalyst. The isomerization catalyst was a platinum containing chloride alumina. Table 5 summarizes the PIONA data of the iso-paraffin rich stream and the reverse isomerate fraction.

TABLE 5

| Example 1 Stream Data from Reverse Isomerization | | |
|---|---|---|
| Stream | First iso-paraffin rich stream | Reverse-isomerate fraction |
| n-paraffins, wt. % | 0.51 | 43.45 |
| iso-paraffins, wt. % | 43.47 | 18.47 |
| Naphthenes, wt. % | 50.11 | 34.06 |
| Aromatics, wt. % | 5.92 | 4.02 |

As shown in Table 5, the reverse isomerization step increases a concentration of the n-paraffins from 0.51 wt. % to 43.45 wt. % after treating the first iso-paraffin stream in the reverse isomerization unit.

Example 2

The reverse isomerate fraction of Example 1 was recycled in the system and added to the hydrocrackate fraction of Comparative Example 1 to form a combined fraction. The combined fraction comprising the hydrocrackate fraction and the reverse isomerate fraction was subjected to an n-paraffin separation step as described in Comparative Example 2 to produce a second n-paraffin rich stream and a second iso-paraffin rich stream. Table 6 summarizes the PIONA data of the second n-paraffin rich stream and the second iso-paraffin rich stream.

TABLE 6

| Example 2 Stream Data from Separation of Combined Fraction | | |
|---|---|---|
| Stream | Second n-paraffin rich stream | Second iso-paraffin rich stream |
| n-paraffins, wt. % | 41.42 | 0.29 |
| iso-paraffins, wt. % | 1.06 | 24.82 |
| Naphthenes, wt. % | 0.58 | 28.61 |

TABLE 6-continued

| Example 2 Stream Data from Separation of Combined Fraction | | |
|---|---|---|
| Stream | Second n-paraffin rich stream | Second iso-paraffin rich stream |
| Aromatics, wt. % | 0.07 | 3.38 |
| Total wt. % | 43.13 | 57.10 |

As shown in Table 6, recycling the reverse isomerate fraction and combining the reverse isomerate fraction with the hydrocrackate fraction to form the combined fraction, and subsequently separating n-paraffins from the combined fraction results in 41.42 wt. % of n-paraffins from the process, relative to the total weight of the hydrocrackate fraction. The methods and systems described herein significantly increase the concentration of n-paraffins produced in comparison to Comparative Example 1 (14.24 wt. % n-paraffins produced, relative to the total weight of the hydrocrackate fraction), which did not include reverse-isomerization and recycling steps. Therefore, the resulting product streams provide desirable value-added compositions.

A first aspect of the present disclosure is directed to a process for treating a diesel feedstock to convert diesel to n-paraffins, the process comprising hydrodesulfurizing and hydrodenitrogenizing the diesel feedstock to reduce a sulfur content of the diesel feedstock and a nitrogen content of the diesel feedstock, hydrocracking the hydrodesulfurized and hydrodenitrogenized diesel feedstock over a metal-containing diesel hydrocracking catalyst comprising at least one zeolite to produce a hydrocrackate fraction, separating the hydrocrackate fraction into a first stream enriched in n-paraffins and a second stream enriched in iso-paraffins and naphthenes, and reverse isomerizing at least a portion of the second stream over an isomerization catalyst to convert at least a portion of the iso-paraffins to n-paraffins, producing a reverse isomerate fraction.

A second aspect of the present disclosure may include the first aspect, further comprising separating the reverse isomerate fraction into a third stream enriched in n-paraffins and a fourth stream enriched in iso-paraffins and naphthenes.

A third aspect of the present disclosure may include either one of the first or second aspect, further comprising recycling at least a portion of the reverse isomerate fraction.

A fourth aspect of the present disclosure may include any one of the first through third aspects, further comprising combining at least a portion of the hydrocrackate fraction and at least a portion of the reverse isomerate fraction.

A fifth aspect of the present disclosure may include any one of the first through fourth aspects, wherein the third stream comprises at least a portion of the first stream from the hydrocrackate fraction and n-paraffins from the reverse isomerate fraction.

A sixth aspect of the present disclosure may include any one of the first through fifth aspects, wherein the third stream comprises greater than or equal to 80 weight percent n-paraffins, based on the total weight of the third stream.

A seventh aspect of the present disclosure may include any one of the first through sixth aspects, wherein the third stream comprises greater than or equal to 30 weight percent n-paraffins, based on the total weight of the hydrocrackate fraction.

An eighth aspect of the present disclosure may include any one of the first through seventh aspects, further comprising steam cracking at least a portion of the first stream, at least a portion of the third stream, or at least a portion of the first stream and at least a portion of the third stream to convert at least a portion of the n-paraffins to light olefins.

A ninth aspect of the present disclosure may include any one of the first through eighth aspects, wherein the fourth stream comprises at least a portion of the second stream from the hydrocrackate fraction and iso-paraffins from the reverse isomerate fraction.

A tenth aspect of the present disclosure may include any one of the first through ninth aspects, further comprising adding at least a portion of the second stream, at least a portion of the fourth stream, or at least a portion of the second stream and at least a portion of the fourth stream to a gasoline pool.

An eleventh aspect of the present disclosure may include any one of the first through tenth aspects, further comprising adding at least a portion of the second stream, at least a portion of the fourth stream, or at least a portion of the second stream and at least a portion of the fourth stream to a feedstock for a fluid catalytic cracking process or a catalytic reforming process.

A twelfth aspect of the present disclosure may include the eleventh aspect, wherein the fluid catalytic cracking process converts at least a portion of the feedstock for the fluid catalytic cracking process to propylene.

A thirteenth aspect of the present disclosure may include any one of the first through twelfth aspects, further comprising removing at least a portion of $C_1$-$C_4$ hydrocarbons from the reverse isomerate fraction.

A fourteenth aspect of the present disclosure may include any one of the first through fourteenth aspects, wherein the sulfur content of the diesel feedstock is reduced to less than or equal to 500 ppm by weight in the hydrodesulfurizing step A fifteenth aspect of the present disclosure may include any one of the first through fourteenth aspects, wherein the diesel feedstock boils at a temperature from 150° C. to 420° C.

A sixteenth aspect of the present disclosure may include any one of the first through fifteenth aspects, wherein the metal-containing diesel hydrocracking catalyst comprises a noble metal selected from the group consisting of platinum, palladium, ruthenium, gold, and a combination of two or more thereof.

A seventeenth aspect of the present disclosure may include any one of the first through sixteenth aspects, wherein the hydrocracking occurs in a hydrocracking reactor that operates at a temperature from 280° C. to 400° C., at pressure less than or equal to 60 bars, a hydrogen-to-oil ratio of from 500 StLt/Lt to 1000 StLt/Lt, and at a liquid hourly space velocity from 0.5 per hour to 5 per hour.

An eighteenth aspect of the present disclosure may include any one of the first through seventeenth aspects, wherein the at least one zeolite comprises at least one of an ultra-stable Y-type (USY) zeolite, a post modified USY zeolite, a zeolite beta (BEA zeolite), an MFI zeolite, or an MOR zeolite.

A nineteenth aspect of the present disclosure may include any one of the first through eighteenth aspects, wherein the isomerization catalyst comprises platinum, chlorinated alumina, sulfated zirconia, mordenite framework zeolite (MOR), or combinations of two or more thereof.

A twentieth aspect of the present disclosure may include any one of the first through nineteenth aspects, wherein the isomerizing occurs in a reactor that operates at a temperature from 80° C. to 300° C., at pressure of from 15 bars to 35 bars, and at a liquid hourly space velocity from 1 per hour to 2 per hour.

It is noted that recitations in the present disclosure of a component of the present disclosure being "operable" or "sufficient" in a particular way, to embody a particular property, or to function in a particular manner, are structural recitations, as opposed to recitations of intended use. More specifically, the references in the present disclosure to the manner in which a component is "operable" or "sufficient" denotes an existing physical condition of the component and, as such, is to be taken as a definite recitation of the structural characteristics of the component.

Having described the subject matter of the present disclosure in detail and by reference to specific embodiments, it is noted that the various details disclosed in the present disclosure should not be taken to imply that these details relate to elements that are essential components of the various embodiments described in the present disclosure. Further, it will be apparent that modifications and variations are possible without departing from the scope of the present disclosure, including, but not limited to, embodiments defined in the appended claims.

The singular forms "a", "an" and "the" include plural referents, unless the context clearly dictates otherwise.

Throughout this disclosure ranges are provided. It is envisioned that each discrete value encompassed by the ranges are also included. Additionally, the ranges which may be formed by each discrete value encompassed by the explicitly disclosed ranges are equally envisioned.

As used in this disclosure and in the appended claims, the words "comprise," "has," and "include" and all grammatical variations thereof are each intended to have an open, non-limiting meaning that does not exclude additional elements or steps.

As used in this disclosure, terms such as "first" and "second" are arbitrarily assigned and are merely intended to differentiate between two or more instances or components. It is to be understood that the words "first" and "second" serve no other purpose and are not part of the name or description of the component, nor do they necessarily define a relative location, position, or order of the component. Furthermore, it is to be understood that that the mere use of the term "first" and "second" does not require that there be any "third" component, although that possibility is contemplated under the scope of the present disclosure.

What is claimed is:

1. A process for treating a diesel feedstock to convert diesel to n-paraffins, comprising:
   hydrodesulfurizing and hydrodenitrogenizing the diesel feedstock to reduce a sulfur content of the diesel feedstock and a nitrogen content of the diesel feedstock;
   hydrocracking the hydrodesulfurized and hydrodenitrogenized diesel feedstock over a metal-containing diesel hydrocracking catalyst comprising at least one zeolite to produce a hydrocrackate fraction;
   separating the hydrocrackate fraction into a first stream enriched in n-paraffins and a second stream enriched in iso-paraffins and naphthenes; and
   reverse isomerizing at least a portion of the second stream over an isomerization catalyst to convert at least a portion of the iso-paraffins to n-paraffins, producing a reverse isomerate fraction.

2. The process of claim 1, further comprising separating the reverse isomerate fraction into a third stream enriched in n-paraffins and a fourth stream enriched in iso-paraffins and naphthenes.

3. The process of claim 2, further comprising recycling at least a portion of the reverse isomerate fraction.

4. The process of claim 2, further comprising combining at least a portion of the hydrocrackate fraction and at least a portion of the reverse isomerate fraction.

5. The process of claim 2, wherein the third stream comprises at least a portion of the first stream from the hydrocrackate fraction and n-paraffins from the reverse isomerate fraction.

6. The process of claim 2, wherein the third stream comprises greater than or equal to 80 weight percent n-paraffins, based on the total weight of the third stream.

7. The process of claim 2, wherein the third stream comprises greater than or equal to 30 weight percent n-paraffins, based on the total weight of the hydrocrackate fraction.

8. The process of claim 2, further comprising steam cracking at least a portion of the first stream, at least a portion of the third stream, or at least a portion of the first stream and at least a portion of the third stream to convert at least a portion of the n-paraffins to light olefins.

9. The process of claim 2, wherein the fourth stream comprises at least a portion of the second stream from the hydrocrackate fraction and iso-paraffins from the reverse isomerate fraction.

10. The process of claim 2, further comprising adding at least a portion of the second stream, at least a portion of the fourth stream, or at least a portion of the second stream and at least a portion of the fourth stream to a gasoline pool.

11. The process of claim 2, further comprising adding at least a portion of the second stream, at least a portion of the fourth stream, or at least a portion of the second stream and at least a portion of the fourth stream to a feedstock for a fluid catalytic cracking process or a catalytic reforming process.

12. The process of claim 11, wherein the fluid catalytic cracking process converts at least a portion of the feedstock for the fluid catalytic cracking process to propylene.

13. The process of claim 1, further comprising removing at least a portion of $C_1$-$C_4$ hydrocarbons from the reverse isomerate fraction.

14. The process of claim 1, wherein the sulfur content of the diesel feedstock is reduced to less than or equal to 500 ppm by weight in the hydrodesulfurizing step.

15. The process of claim 1, wherein the diesel feedstock boils at a temperature from 150° C. to 420° C.

16. The process of claim 1, wherein the metal-containing diesel hydrocracking catalyst comprises a noble metal selected from the group consisting of platinum, palladium, ruthenium, gold, and a combination of two or more thereof.

17. The process of claim 1, wherein the hydrocracking occurs in a hydrocracking reactor that operates at a temperature from 280° C. to 400° C., at pressure less than or equal to 60 bars, a hydrogen-to-oil ratio of from 500 StLt/Lt to 1000 StLt/Lt, and at a liquid hourly space velocity from 0.5 per hour to 5 per hour.

18. The process of claim 1, wherein the at least one zeolite comprises at least one of an ultra-stable Y-type (USY) zeolite, a post modified USY zeolite, a zeolite beta (BEA zeolite), an MFI zeolite, or an MOR zeolite.

19. The process of claim 1, wherein the isomerization catalyst comprises platinum, chlorinated alumina, sulfated zirconia, mordenite framework zeolite (MOR), or combinations of two or more thereof.

20. The process of claim 1, wherein the isomerizing occurs in a reactor that operates at a temperature from 80° C. to 300° C., at pressure of from 15 bars to 35 bars, and at a liquid hourly space velocity from 1 per hour to 2 per hour.

\* \* \* \* \*